(12) United States Patent
Burioni et al.

(10) Patent No.: US 9,587,011 B2
(45) Date of Patent: Mar. 7, 2017

(54) MONOCLONAL ANTIBODIES CAPABLE OF REACTING WITH A PLURALITY OF INFLUENZA VIRUS A SUBTYPES

(71) Applicant: Pomona Ricerca S.r.l., Turin (IT)

(72) Inventors: Roberto Burioni, Rimini (IT); Massimo Clementi, Milan (IT)

(73) Assignee: Pomona Ricerca S.r.l., Turin (IT)

( * ) Notice: Subject to any disclaimer, the term of this patent is extended or adjusted under 35 U.S.C. 154(b) by 0 days.

(21) Appl. No.: 14/938,101

(22) Filed: Nov. 11, 2015

(65) Prior Publication Data

US 2016/0060325 A1   Mar. 3, 2016

Related U.S. Application Data

(62) Division of application No. 12/922,850, filed as application No. PCT/IB2009/051068 on Mar. 16, 2009, now Pat. No. 9,200,063.

(30) Foreign Application Priority Data

Mar. 17, 2008 (IT) .............. TO2008A0204

(51) Int. Cl.
| | |
|---|---|
| C12N 15/74 | (2006.01) |
| C07K 16/10 | (2006.01) |
| A61K 47/48 | (2006.01) |
| C07K 16/42 | (2006.01) |
| G01N 33/68 | (2006.01) |

(52) U.S. Cl.
CPC ...... *C07K 16/1018* (2013.01); *A61K 47/4853* (2013.01); *C07K 16/4216* (2013.01); *C12N 15/74* (2013.01); *G01N 33/686* (2013.01); *C07K 2316/96* (2013.01); *C07K 2317/21* (2013.01); *C07K 2317/24* (2013.01); *C07K 2317/33* (2013.01); *C07K 2317/34* (2013.01); *C07K 2317/54* (2013.01); *C07K 2317/55* (2013.01); *C07K 2317/56* (2013.01); *C07K 2317/622* (2013.01); *C07K 2317/76* (2013.01); *G01N 2469/00* (2013.01)

(58) Field of Classification Search
None
See application file for complete search history.

(56) References Cited

U.S. PATENT DOCUMENTS

| | | | |
|---|---|---|---|
| 4,946,778 A | 8/1990 | Ladner et al. | |
| 5,245,015 A | 9/1993 | Fung et al. | |
| 6,057,421 A | 5/2000 | Muller et al. | |
| 6,964,199 B2 | 11/2005 | Lee et al. | |
| 9,200,063 B2* | 12/2015 | Burioni .............. | C07K 16/1018 |
| 2003/0100741 A1 | 5/2003 | Muller et al. | |
| 2004/0224310 A1 | 11/2004 | McGready | |
| 2005/0080240 A1 | 4/2005 | Kunert et al. | |
| 2005/0221298 A1 | 10/2005 | Muller et al. | |
| 2008/0014205 A1* | 1/2008 | Horowitz ........... | C07K 16/1018 424/159.1 |

FOREIGN PATENT DOCUMENTS

| | | |
|---|---|---|
| EP | 0621339 A2 | 10/1994 |
| EP | 0675199 A2 | 10/1995 |
| WO | 84/00687 A1 | 3/1984 |
| WO | 92/15885 A1 | 9/1992 |
| WO | 94/09136 A1 | 4/1994 |
| WO | WO9409136 * | 4/1994 |
| WO | 00/05266 A1 | 2/2000 |
| WO | 02/46235 A1 | 6/2002 |
| WO | 02/055560 A2 | 7/2002 |
| WO | 03/064473 A2 | 8/2003 |
| WO | 2007/134327 A2 | 11/2007 |
| WO | 2008/033159 A1 | 3/2008 |
| WO | 2008/093280 A2 | 8/2008 |
| WO | 2009/037297 A2 | 3/2009 |
| WO | 2009/115972 A1 | 9/2009 |
| WO | 2009/144667 A1 | 12/2009 |
| WO | 2010/073204 A1 | 7/2010 |
| WO | 2010/140114 A1 | 12/2010 |
| WO | 2011/117848 A1 | 9/2011 |

OTHER PUBLICATIONS

Burioni et al., Monoclonal antibodies isolated from human B cells neutralize a broad range of H1 subtype influenza A viruses including swine-origin Influenza virus (S-OIV), 2010, Virology, vol. 399, pp. 144-152.*

Vajdos et al., Comprehensive Functional Maps of the Antigenbinding Site of an Anti-ErbB2 Antibody Obtained with Shotgun Scanning Mutagenesis, 2002, Journal of Molecular Biology, vol. 320, pp. 415-428.*

PCT International Search Report and the Written Opinion, Application No. PCT/IB2009/051068 filed Mar. 16, 2009, dated Aug. 31, 2009.

PCT International Search Report and the Written Opinion, Application No. PCT/IB2009/052212 filed May 27, 2009, dated Sep. 28, 2009.

PCT International Search Report and the Written Opinion, Application No. PCT/IB2009/055867 filed Dec. 21, 2009, dated Mar. 31, 2010.

PCT International Search Report and the Written Opinion, Application No. PCT/IB2010/052434 filed Jun. 1, 2010, dated Sep. 14, 2010.

(Continued)

*Primary Examiner* — Benjamin P Blumel
(74) *Attorney, Agent, or Firm* — MacMillan, Sobanski & Todd, LLC

(57) ABSTRACT

Monoclonal antibodies directed against the influenza A virus are described, which have the advantageous and unpredicted property of being able to bind a plurality of subtypes of the influenza A virus. One preferred embodiment is the antibody designated as Fab28, which displays a neutralizing activity against a plurality of subtypes of the influenza A virus. Anti-idiotype antibodies directed against the monoclonal antibodies of the invention, immunogenic or vaccine compositions comprising the monoclonal antibodies of the invention are also described, as well as therapeutic, prophylactic and diagnostic applications for the monoclonal antibodies of the invention. The monoclonal antibodies of the invention can also be used for testing antibody preparations to be used as vaccines.

9 Claims, 2 Drawing Sheets

(56) References Cited

OTHER PUBLICATIONS

US Final Office Action, U.S. Appl. No. 12/524,816, filed Jul. 28, 2009, dated May 9, 2012.
US Final Office Action, U.S. Appl. No. 13/141,071, filed Jun. 20, 2011, dated Jul. 25, 2013.
US Notice of Allowance, U.S. Appl. No. 12/524,816, filed Jul. 28, 2009, dated Oct. 4, 2012.
US Notice of Allowance, U.S. Appl. No. 13/141,071, filed Jun. 20, 2011, dated Sep. 6, 2013.
US Notice of Allowance, U.S. Appl. No. 13/265,542, filed Oct. 20, 2011, dated Mar. 22, 2013.
US Non-Final Office Action, U.S. Appl. No. 12/524,816, filed Jul. 28, 2009, dated Jul. 21, 2011.
US Non-Final Office Action, U.S. Appl. No. 12/994,746, filed Nov. 24, 2010, dated Jul. 30, 2014.
US Non-Final Office Action, U.S. Appl. No. 12/994,746, filed Nov. 24, 2010, dated Oct. 11, 2013.
US Non-Final Office Action, U.S. Appl. No. 12/994,746, filed Nov. 24, 2010, dated Dec. 5, 2012.
US Non-Final Office Action, U.S. Appl. No. 13/141,071, filed Jun. 20, 2011, dated Mar. 9, 2012.
US Non-Final Office Action, U.S. Appl. No. 13/141,071, filed Jun. 20, 2011, dated Nov. 19, 2012.
US Non-Final Office Action, U.S. Appl. No. 13/265,542, filed Oct. 20, 2011, dated Oct. 25, 2012.
US Restriction Requirement, U.S. Appl. No. 12/524,816, filed Jul. 28, 2009, dated Apr. 5, 2011.
US Restriction Requirement, U.S. Appl. No. 13/141,071, filed Jun. 20, 2011, dated Nov. 14, 2011.
US Restriction Requirement, U.S. Appl. No. 13/265,542, filed Oct. 20, 2011, dated Aug. 28, 2012.
McMichael, "HIV Vaccines", The Annual Review of Immunology, 2006, vol. 24, pp. 227-255.
Medimmune, "FluMist", 2010, Package Insert, pp. 1-22.
Merriam-Webster, "Definition of Disparage", Web Article, Retrieved 2016, www.merriam-webster.com/dictionary/disparage.
Merriam-Webster, "Definition of Pathology", Web Article, Retrieved 2016, www.merriam-webster.com/dictionary/pathology.
Merriam-Webster, "Definition of Prophylactic", Web Article, Retrieved 2016, www.merriam-webster.com/dictionary/prophylactic.
Merriam-Webster, Definition of Syndrome Web Article, Retrieved 2016, www.merriam-webster.com/dictionary/syndrome.
Molinari et al., "The annual impact of seasonal influenza in the US: Measuring disease burden and costs", Vaccine, 2007, vol. 25, pp. 5086-5096.
Montefiori, "Neutralizing antibodies take a swipe at HIV in vivo", Nature Medicine, 2005, vol. 11, No. 6, pp. 593-594.
Müller et al., "Generation and specificity of monoclonal anti-idiotypic antibodies against human HIV-specific antibodies. I. Cross-reacting idiotopes are expressed in subpopulations of HIV-infected individuals", The Journal of Immunology, 1991, vol. 147, pp. 933-941.
Müller et al., "Stimulation of Antiviral Antibody Response in SHIV-IIIB-Infected Macaques", Scandinavian Journal of Immunology, 2001, vol. 54, pp. 383-395.
Müller et al., "Stimulation of HIV-1-neutralizing antibodies in simian HIV-IIIB-infected macaques", Proceedings of the National Academy of Sciences (PNAS), 1998, vol. 95, pp. 276-281.
Nguyen et al., "Heterosubtypic Immunity to Influenza A Virus Infection Requires B Cells by Not CD8+ Cytotoxic T Lymphocytes", The Journal of Infectious Diseases, 2001, vol. 183, pp. 368-376.
NIH AIDS Reagent Program, "About the Program", Web Article, Retrieved 2016, http://www.aidsreagent.org/about_program.cfm.
NIH AIDS Reagent Program, "Reagent Information: U87 CD4+ Cells", Web Article, Retrieved 2016, http://www.aidsreagent.org/reagentdetail.cfm?t=cell_lines&id=20.
Oxford University Press, "Virus Culture—A Practical Approach", Edited by A.J. Cann, 2000, pp. 82-87.

Padlan et al., "Identification of specificity-determining residues in antibodies", The FASEB Jouranl, 1995, vol. 9, pp. 133-139.
Pantophlet et al., "GP120: Target for Neutralizing HIV-1 Antibodies", The Annual Review of Immunology, 2006, vol. 24, pp. 739-769.
Perotti et al., "Identification of a Broadly Cross-Reacting and Neutralizing Human Monoclonal Antibody Directed against the Hepatitis C Viruse E2 Protein", Journal of Virology, 2008, vol. 82, No. 2, pp. 1047-1052.
Rangel-Moreno et al., "B Cells Promote Resistance to Heterosubtypic Strains of Influenza via Multiple Mechanisms", The Journal of Immunology, 2008, vol. 180, pp. 454-463.
Rosa et al., "A quantitative test to estimate neutralizing antibodies to the hepatitis C virus: Cytofluorimetric assessment of envelope glycoprotein 2 binding to target cells", Proceedings of the National Academy of Sciences (PNAS), 1996, vol. 93, pp. 1759-1763.
Rudikoff et al., "Single amino acid substitution altering antigen-binding specificity", Proceedings of the National Academy of Sciences (PNAS), 1982, vol. 79, pp. 1979-1983.
Sanofi Pasteur, "Fluzone", Package Insert, pp. 1-24.
Sigma-Aldrich, "Ribavirin—Antiviral", Product Specification, Web Article, Retrieved 2016, pp. 1-4.
Smirnov et al., "An Epitope Shared by the Hemagglutinins of H1, H2, H5, and H6 Subtypes of Influenza A Virus", Acta Virologica, 1999, vol. 43, No. 4, pp. 237-244.
Smirnov et al., "Prevention and treatment of bronchopneumonia in mice caused by mouse-adapted variant of avian H5N2 influenza A virus using monoclonal antibody against conserved epitope in the HA stem region", Archives of Virology, 2000, vol. 145, pp. 1733-1741.
Stamatatos et al., "Neutralizing antibodies generated during natural HIV-1 infection: good news for an HIV-1 vaccine?", Nature Medicine, 2009, vol. 15, No. 8, pp. 866-870.
Staprans et al., "The roles of nonhuman primates in the preclinical evaluation of candidate AIDS vaccines", Expert Review of Vaccines, 2004, vol. 3, No. 4, pp. 5-32.
Sui et al., "Structural and Functional Bases for Broad-Spectrum Neutralization of Avian and Human Influenza A Viruses", Nature Structural and Molecular Biology, 2009, vol. 16, No. 3, pp. 265-273.
Surveillance Report, "Influenza Surveillance in Europe Sep. 2008", European Center for Disease Prevention and Control (ECDC), 2010, pp. 1-24.
Tarr et al., "Characterization of the Hepatitis C Virus E2 Epitope Defined by the Broadly Neutralizing Monoclonal Antibody AP33", Hepatology, 2006, vol. 43, pp. 592-601.
Tarr et al., "Determination of the human antibody response to the epitope defined by the hepatitus C virus-neutralizing monoclonal antibody AP33", Journal of General Virology, 2007, vol. 88, pp. 2991-3001.
Thompson et al., "Mortality Associated with Influenza and Respiratory Syncytial Virus in the United States", JAMA, 2003, vol. 289, No. 2, pp. 179-186.
Throsby et al., "Heterosubtypic Neutralizing Monoclonal Antibodies Cross-Protective against H5N1 and H1N1 Recovered from Human IgM+ Memory B Cells", PLoS One, 2008, vol. 3, No. 12, pp. 1-15.
Tkacova et al., "Evaluation of Monoclonal Antibodies for Subtyping of Currently Circulating Human Type A Influenza Viruses", Journal of Clinical Microbiology, 1997, vol. 35 No. 5, pp. 1196-1198.
Trkola et al., "Delay of HIV-1 rebound after cessation of antiretroviral therapy through passive transfer of human neutralizing antibodies", Nature Medicine, 2005, vol. 11, No. 6, pp. 615-622.
Vajdos et al., "Comprehensive Functional Maps of the Antigen-binding Site of an Anti-ErbB2 Antibody Obtained with Shotgun Scanning Mutagenesis", Journal of Molecular Biology, 2002, vol. 320, pp. 415-428.
Wang et al., "Human monoclonal and polyclonal anti-human immunodeficiency virus-1 antibodies share a common clonotypic specificity", European Journal of Immunology, 1992, vol. 22, pp. 1749-1755.

(56) References Cited

OTHER PUBLICATIONS

Wang et al., "Identification of an Idiotypic Peptide Recognized by Autoantibodies in Human Immunodeficiency Virus-1-infected Individuals", The Journal of Clinical Investigation, 1995, vol. 96, pp. 775-780.
Ward et al., "Binding activities of a repertoire of single immunoglobulin variable domains secreted from *Escherichia coli*", Nature, 1989, vol. 341, pp. 544-546.
Wikipedia, "Epitope Mapping", Web Article, Retrieved 2016, en.wikipedia.org/wiki/Epitope_mapping.
Wikipedia, "Neutralizing Antibody", Web Article, Retrieved 2014, en.wikipedia.org/wiki/Neutralizing_antibody.
Winkler et al., "Changing the Antigen Binding Specificity by Single Point Mutations of an Anti-p24 (HIV-1) Antibody", The Journal of Immunology, 2000, vol. 165, pp. 4505-4514.
Ziegler et al., "Type- and Subtype-Specific Detection of Influenza Viruses in Clinical Specimens by Rapid Culture Assay", Journal of Clinical Microbiology, 1995, vol. 33, No. 2, pp. 318-321.
European Office Action, Application No. 09722394.5 dated Jun. 2, 2014.
PCT International Preliminary Report on Patentability, Application No. PCT/IB2008/050307 filed Jan. 29, 2008, dated Apr. 30, 2009.
PCT International Preliminary Report on Patentability, Application No. PCT/IB2009/055867 filed Dec. 21, 2009, dated Jun. 29, 2011.
PCT International Preliminary Report on Patentability, Application No. PCT/IB2010/052434 filed Jun. 1, 2010, filed Dec. 6, 2011.
PCT International Search Report, Application No. PCT/IT2003/000032 filed Jan. 29, 2003, dated Aug. 22, 2003.
PCT International Search Report, Application No. PCT/US2001/045221 filed Nov. 30, 2001, dated Mar. 20, 2003.
PCT International Search Report and the Written Opinion, Application No. PCT/IB2008/050307 filed Jan. 29, 2008, dated Sep. 9, 2008.
"2009-2010 Seasonal Influenza Vaccines", published by the US Food and Drug Administration retrieved on Nov. 19, 2014 from http://www.fda.gov/ForConsumers/ConsumerUpdates/ucm100139.htm.
"AIDS Epidemic Update: Special Report in HIV Prevention", United Nations Programme on HIV/AIDS (UNAIDS), 2005, pp. 1-98.
"Types of Vaccines", National Institute of Allergy and Infectious Diseases, Web Article, Retrieved 2014, http://www.niaid.nih.gov/topics/vaccines/understanding/Pages/typesVaccines/aspx.
Allander et al., "Recombinant human monoclonal antibodies against different conformational epitopes of the E2 envelope glycoprotein of hepatitis C virus that inhibits its interaction with CD81", Journal of General Virology, 2000, vol. 81, pp. 2451-2459.
Asanuma et al., "Influenza PR8 HA-specific Fab fragmetns produced by phage display methods", Biochemical and Biophysical Research Communications, 2008, vol. 366, pp. 445-449.
Austin et al., "Antigenic Mapping of an Avian H1 Influenza Virus Haemagglutinin and Interrelationships of H1 Viruses from Humans, Pigs and Birds", Journal of General Virology, 1986, vol. 67, pp. 983-992.
Baca et al., "Antibody Humanization Using Monovalent Phage Display", The Journal of Biological Chemistry, 1997, vol. 272, No. 16, pp. 10678-10684.
Bansal, "A summary of the workshop on Passive Immunization Using Monoclonal Antibodies for HIV/AIDS: Held at the National Institute of Allergy and Infectious Diseases, Bethesda on Mar. 10, 2006", Biologicals, 2007, vol. 35, No. 4, pp. 367-371.
Boudet et al., "Anti-Idiotypic Antibodies to the Third Variable Domain of gp120 Induce an Anti-HIV-1 Antibody Response in Mice", Virology, 1994, vol. 200, pp. 176-188.
Braibant et al., "Antibodies to conserved epitopes of the HIV-1 envelope in sera from long-term non-progressors: prevalences and association with neutralizing activity", AIDS, 2006, vol. 20, No. 15, pp. 1923-1930.

Bugli et al., "Mapping B-Cell Epitopes of Hepatitis C Virus E2 Glycoprotein Using Human Monoclonal Antibodies from Phage Display Libraries", Journal of Virology, 2001, vol. 75, No. 20, pp. 9986-9990.
Burioni et al., "A vector for the expression of recombinant monoclonal Fab fragments in bacteria", Journal of Immunological Methods, 1998, vol. 217, pp. 195-199.
Burioni et al., "Anti-HIV-1 Response Elicited in Rabbits by Anti-Idiotype Monoclonal Antibodies Mimicking the CD4-Binding Site", PLoS One, 2008, vol. 3, No. 10, pp. 1-7.
Burioni et al., "Cross-reactive pseudovirus-neutralizing anti-envelope antibodies coexist with antibodies devoid of such activity in persistent hepatitis C virus infection", Virology, 2004, vol. 327, pp. 242-248.
Burioni et al., "Dissection of Human Humoral Immune Response Against Hepatitis C Virus E2 Glycoprotein by Repertoire Cloning and Generation of Recombinant Fab Fragements", Hepatology, 1998, vol. 28, pp. 810-814.
Burioni et al., "Molecular cloning of the first human monoclonal antibodies neutralizing with high potency Swine-origin Influenza A pandemic virsu (S-OIV)", New Microbiologica, 2009, vol. 32, pp. 319-324.
Burioni et al., "Monoclonal antibodies isolated from human B cells neutralize a broad range of H1 subtype influenza A viruses including swine-origin Influenza virus (S-OIV)", Virology, 2010, vol. 399, pp. 144-152.
Burioni et al., "Nonneutralizing Human Antibody Fragments against Hepatitis C Virus E2 Glycoprotein Modulate Neutralization of Binding Activity of Human Recombinant Fabs", Virology, 2001, vol. 288, pp. 29-35.
Burioni, "I Treponemi Instestinali Umani: Tesi per il conseguimento del dottorato di ricera in scienze microbiologichi di", 1993, Italian Text, pp. 1-164.
Burton et al., "Human Primers for Fab Amplification: Original Set", Phage Display Manual, 2001, A1.6-A1.7, Appendix 1, p. 1.
Burton et al., "Mouse Primers for Fab Amplification", Phage Display Manual, 2001, A1.10, Appendix 1, p. 1.
Burton et al., "Vaccines and the induction of functional antibodies: Time to look beyond the molecules of natural Infections?", Nature Medicine, 2000, vol. 6, No. 2, pp. 123-125.
Burton, "Antibodies, viruses and vaccines", Nature Review, Immunology, 2002, vol. 2, pp. 706-713.
Carter et al., "Humanization of an anti-p185HER2 antibody for human cancer therapy", Proceedings of the National Academy of Sciences (PNAS), 1992, vol. 89, pp. 4285-4289.
Chen et al., "Enhancement and destruction of antibody function by somatic mutation: unequal occurrence is controlled by V gene combinatorial associations", The EMBO Journal, 1995, vol. 14, No. 12, pp. 2784-2794.
Cole et al., "A Strategy for the Production of Human Monoclonal Antibodies Reactive with Lung Tumor Cell Lines", Cance Research, 1984, vol. 44, pp. 2750-2753.
Creeke et al., "Clinical testing for neutralizing antibodies to interferon-β in multiple sclerosis", Therapeutic Advances in Neurological Disorders, 2013, vol. 6, No. 1, pp. 3-17.
Eren et al., "Preclinical Evaluation of Two Neutralizing Human Monoclonal Antibodies against Hepatitis C Virus (HCV): a Potential Treatment to Prevent HCV Reinfection in Liver Transplant Patients", Journal of Virology, 2006, vol. 80, No. 6, pp. 2654-2664.
Freedman, "The Role of Neutralizing Antibodies in MS Treatements", Medscape Neurology, 2003, vol. 5, No. 2, pp. 1-3.
Geretti, "Antiretroviral Resistance in Clinical Practice", Mediscript, 2006, Chapter 12, pp. 1-11.
Goldstein et al., "Effect of Formalin, β-Propiolactone, Merthiolate, and Ultraviolet Light Upon Influenza Virus Infectivity, Chicken Cell Agglutination, Hemagglutination, and Antigenicity", Applied Microbiology, 1970, vol. 19, No. 2, pp. 290-294.
Grant et al., "The anti-idiotypic antibody 1F7 selectively inhibits cytotoxic T cells activated in HIV-1 infection", Immunology and Cell Biology, 2000, vol. 78, pp. 20-27.
Gussow et al., "Humanization of monoclonal antibodies", Methods of Enzymology, 1991, vol. 203, pp. 99-121.

(56) References Cited

OTHER PUBLICATIONS

Haigwood, "Predictive Value of Primate Models for AIDS", AIDS Reviews, 2004, vol. 6, pp. 187-198.
Hariharan et al., "Analysis of the Cross-Reactive Anti-gp120 Antibody Population in Human Immunodeficiency Virus-Infected Asymptomatic Individuals", Journal of Virology, 1993, vol. 67, No. 2, pp. 953-960.
Hedestam et al., "The challenges of eliciting neutralizing antibodies to HIV-1 and to influenza virus", Nature Review, Microbiology, 2008, vol. 6, pp. 143-155.
Hernandez et al., "Compared protective effect of nasal immunoprophylaxis using a new human monoclonal IgM antibody, human polyclonal antibodies, F(ab')2 amantadine, and zanamivir for prophylaxis of influenza A virus pneumonia in mice", Military Medicine, 2003, vol. 168, No. 3, p. 246.
Holm et al., "Functional mapping and single chain construction of the anti-cytokeratin 8 monoclonal antibody TS1", Molecular Immunology, 2007, vol. 44, pp. 1075-1084.
Humbert et al., "Mimotopes selected with antibodies from HIV-1-neutralizing long-term non-progresser plasma", European Journal of Immunology, 2007, vol. 37, pp. 501-515.
Invitrogen, "pcDNA 3.1(+), pcDNA(−)" User Manual, Version K, 2010, pp. 1-23.
Johansson et al., "Human combinatorial libraries yield rare antibodies that broadly neutralize hepatitis C virus", Proceedings of the National Academy of Sciences (PNAS), 2007, vol. 104, No. 41, pp. 16269-16274.
Kasai et al., "Molecular cloning of murine monoclonal anti-idiotypic Fab", Journal of Immunological Methods, 1992, vol. 155, pp. 77-89.
Knight et al., "Stable expression of cloned human antibody genes in murine myeloma cells", Human Antibodies and Hybridomas, 1992, vol. 3, No. 3, pp. 129-136, Abstract Only.
Kunert et al., "Molecular Characterization of Five Neutralizing Anti-HIV Type 1 Antibodies: Identification of Nonconventional D Segments in the Human Monoclonal Antibodies 2G12 and 2F5", AIDS Research and Human Retroviruses, 1998, vol. 14, No. 13, pp. 1115-1128.
Levy et al., "Targeted Delivery of Ribavirin Improves Outcome of Murine Viral Fulminant Hepatitis via Enhanced Anti-Viral Activity", Hepatology, 2006, vol. 43, pp. 581-591.
Li et al., "Preparation of Anti-Idiotypic Antibody against Avian Influenza Virus Subtype H9", Cellular and Molecular Immunology, 2005, vol. 2, No. 2, pp. 155-157.
MacCallum et al., "Antibody-antigen Interactions: Contact Analysis and Binding Site Topography", Journal of Molecular Biology, 1996, vol. 262, pp. 732-745.
Mancini et al., "Modulation of Epitope-Specific Anti-Hepatitis C Virus E2 (Anti-HCV/E2) Antibodies by Anti-Viral Treatment", Journal of Medical Virology, 2006, vol. 78, pp. 1304-1311.
Mariuzza et al., "The Structural Basis of Antigen-Antibody Recognition", Annual Review of Biophysics and Biophysical Chemistry, 1987, vol. 16, pp. 139-159.
Matsuura et al., "Characterization of Pseudotype VSV Possessing HCV Envelope Proteins", Virology, 2001, vol. 286, pp. 263-275.

\* cited by examiner

SEQUENCE LISTING

<160> NUMBER OF SEQ ID NOS: 5

<210> SEQ ID NO 1
<211> LENGTH: 122
<212> TYPE: PRT
<213> ORGANISM: Homo sapiens

<400> SEQUENCE: 1

```
Leu Glu Glu Ser Gly Gly Gly Val Val Gln Pro Gly Arg Ser Leu Arg
1               5                   10                  15

Leu Ser Cys Ala Ala Ser Gly Phe Pro Phe Ser Ser Tyr Gly Met His
            20                  25                  30

Trp Val Arg Gln Ala Pro Gly Lys Gly Leu Glu Trp Val Ala Gly Val
        35                  40                  45

Ser Tyr Asp Gly Ser Tyr Lys Tyr Tyr Ala Asp Ser Val Lys Gly Arg
    50                  55                  60

Phe Thr Ile Ser Arg Asp Ser Ser Lys Ser Thr Leu Tyr Leu Gln Met
65                  70                  75                  80

Asn Ser Leu Arg Pro Glu Asp Thr Ala Val Tyr Tyr Cys Ala Arg Pro
                85                  90                  95
```

Ser Ala Ile Phe Gly Ile Tyr Ile Ile Leu Asn Gly Leu Asp Val Trp
            100                 105                 110

Gly Gln Gly Thr Thr Val Thr Val Ser Ser
            115                 120

<210> SEQ ID NO 2
<211> LENGTH: 105
<212> TYPE: PRT
<213> ORGANISM: Homo sapiens

<400> SEQUENCE: 2

Glu Leu Thr Gln Ser Pro Ser Ser Val Ser Ala Ser Val Gly Asp Arg
1               5                   10                  15

Val Thr Ile Thr Cys Arg Ala Thr Gln Gly Ile Ser Ser Trp Leu Ala
            20                  25                  30

Trp Tyr Gln Gln Lys Pro Gly Lys Pro Pro Lys Leu Leu Ile Phe Gly
            35                  40                  45

Ala Ser Ser Leu Gln Ser Gly Val Pro Ser Arg Phe Ser Gly Ser Gly
        50                  55                  60

Ser Gly Thr Asp Phe Thr Leu Thr Ile Ser Ser Leu Gln Pro Glu Asp
65                  70                  75                  80

Phe Ala Thr Tyr Phe Cys Gln Gln Ala His Ser Phe Pro Leu Thr Phe
                85                  90                  95

Gly Gly Gly Thr Lys Val Glu Ile Lys
            100                 105

<210> SEQ ID NO 3
<211> LENGTH: 366
<212> TYPE: DNA
<213> ORGANISM: Homo sapiens

<400> SEQUENCE: 3
ctcgaggagt ctgggggagg cgtggtccag cctgggaggt ccctgagact ctcctgtgca    60
gcctctggat tccccttcag tagttatggc atgcactggg tccgccaggc tccaggcaag   120
gggctggagt gggtggcagg tgtttcatat gatggaagtt ataaatacta tgcggactcc   180
gtcaagggcc gattcaccat ctccagagac agttccaaga gcactctata tctgcaaatg   240
aacagcctga cctgagga cacggctgtg tattactgtg cgagaccttc cgcgattttt   300
ggaatataca ttattctaaa cggtttggac gtctggggcc aagggaccac ggtcaccgtc   360
tcttca                                                              366

<210> SEQ ID NO 4
<211> LENGTH: 315
<212> TYPE: DNA
<213> ORGANISM: Homo sapiens

<400> SEQUENCE: 4
gagctcacgc agtctccatc ttccgtgtct gcatctgtag gagacagagt cactatcact    60
tgtcgggcga ctcagggtat tagtagttgg ttagcctggt atcagcagaa accagggaaa   120
ccacctaaac tcctgatttt tggtgcatct agtttgcaaa gtggggtccc atcaaggttc   180
agcggcagtg gatctgggac agatttcact ctcaccatca gcagtctaca gcctgaagat   240
tttgcaactt acttttgtca acaggctcac agtttcccgc tcactttcgg cggcgggacc   300
aaggtggaga tcaaa                                                    315

```
<210> SEQ ID NO 5
<211> LENGTH: 565
<212> TYPE: PRT
<213> ORGANISM: Homo sapiens

<400> SEQUENCE: 5

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Asn Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380
```

-continued

```
Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565
```

MONOCLONAL ANTIBODIES CAPABLE OF REACTING WITH A PLURALITY OF INFLUENZA VIRUS A SUBTYPES

CROSS-REFERENCE TO RELATED APPLICATIONS

This is a divisional application of U.S. Ser. No. 12/922,850 filed Sep. 15, 2010 , now allowed, which is a national stage application filed under 35 USC §371 of international application PCT/IB2009/051068 filed Mar. 16, 2009, which claims the priority to Italian Application Number TO2008A000204 filed Mar. 17, 2008, the entire disclosures of which are expressly incorporated herein by reference.

DESCRIPTION

The present invention in general falls within the field of immunology. More specifically, the invention concerns monoclonal antibodies directed against the HA (hemagglutinin) antigen of the influenza A virus.

BACKGROUND OF THE INVENTION

The annual influenza virus epidemics represent an important cause of morbidity and mortality throughout the world. In the United States of America it is estimated that more than 200,000 people are hospitalized each year for syndromes connected to influenza viruses, with about 40,000 deaths more or less directly related thereto (Thompson et al., JAMA, 2003, 289:179-186). Apart from these figures we must also consider the cases, in exponentially higher numbers, of infected subjects that stay at home for more or less long periods, with inevitable economic repercussions due to the loss of working days. A recent work (Molinari et al., Vaccine, 2007, 25: 5086-5096) has estimated the medical costs directly related to annual epidemics at 10.4 billions of US dollars per year, to which 16.3 billions of US dollars must be added for lost earnings due to absence from work. If in the calculation we consider other items too, such as the monetization of the economical losses linked to the death of the infected subjects, the amount rises to the incredible figure of 87.1 billions of US dollars. These economical data linked with the annual epidemics, together with a dreaded pandemic that could occur at any moment in the near future due to the appearance of influenza viruses new to man, explain the considerable interest in the search for effective strategies to contain the spread of these viruses.

Currently, the only available tool for facing the annual influenza epidemics in some way is an inactivated trivalent vaccine containing viral isolate antigens that presumably will be responsible for the epidemic of the next influenza season. This kind of prediction, based on epidemiological data linked to early isolations in some sentinel geographic areas, does not always turn out to be correct. Thus, there is a not at all negligible risk, which is present year after year, that the trivalent vaccine developed for a certain influenza season might prove substantially ineffective.

In that case, as well as in the case of a new pandemic, the only available prophylactic/therapeutic aid would be to resort to the two available classes of antiviral drugs: the M2 protein inhibitors (amantadine and rimantadine), and the neuraminidase inhibitors (oseltamivir and zanamivir). However, in this situation too, a series of problems can be already expected, related both to the need to administer the antivirals in a very early stage of the infection, and to the rapid appearance, which has already occurred however, of resistant viral isolates.

An alternative effective strategy could be based on neutralizing antibody preparations directed against critical viral proteins and capable of recognizing portions of such proteins which are shared among the different isolates of influenza viruses.

For better understanding of the potential of an approach based on the passive administration of antibodies, it is useful to briefly mention the main structural features of the influenza viruses. The influenza viruses belong to the Orthomyxoviridae family and are characterized by the presence of an envelope derived from infected cell membranes, on which approximately 500 spikes are present, also referred to as projections. Such projections consist of trimers and tetramers from two important viral surface proteins: hemagglutinin (HA) and neuraminidase (NA). An integral membrane protein (M2) is also found on the envelope surface, which protein is present in much lower numbers compared to hemagglutinin and neuraminidase, and also organized in tetramers.

The influenza virus is further characterized by the presence, within the core, of a segmented genome comprised of 8 single stranded RNA fragments. Based on the features of some proteins within the virion (NP and MD, three influenza virus types are recognizable: type A, type B, and type C.

Type A and type B viruses are responsible for the annual epidemics. Instead, type C viruses are responsible for less severe syndromes.

Within type A viruses (the only ones responsible for pandemics and capable of causing the most severe syndromes even during annual epidemics), different subtypes are also recognizable based on the antigenic features of hemagglutinin and neuraminidase. The subtypes that have affected humans in the course of recent history are subtypes H1N1 and H3N2 (still circulating at present and contained in vaccine preparations), as well as subtype H2N2, no longer circulating since 1968 and responsible for the so called "Asiatic" flu in 1957. Other subtypes have sporadically affected humans (H9N2, H7N7, and the so dreaded recent H5N1 subtype), but they have not succeeded in spreading effectively and displacing the circulating subtypes.

The role of the surface proteins is essential in the viral replication cycle. In particular, hemagglutinin is the protein that allows the virus to recognize the sialic acid present on the surface of some cells, and to infect them. Instead, neuraminidase operates at the end of the viral replication cycle, that is during the release of new virus particles from the infected cells. Its function is to assist the release of hemagglutinin of the newly formed virions from the sialic acid present on the surface of the cell that produced them. The key role played by these two proteins, as well as their display on the virus surface, explain why they represent the main target of the immune response, and why they are susceptible to a high rate of mutation. In fact, the annual epidemics are caused by viruses that are more or less different from the ones of the previous years, and therefore are more or less effectively able to escape the immune response they stimulated. In other words, the progressive accumulation of point mutations in hemagglutinin (mostly) and neuraminidase (secondarily) makes the protective antibodies, produced in the course of previous epidemics, on the whole progressively ineffective.

The main protective role within the anti-influenza immune response is played by the humoral component. Antibodies exert their protective role primarily interfering with the binding of hemagglutinin to sialic acid, thereby preventing infection of the cells. Such a selective pressure determines the high rate of mutation in hemagglutinin Sequence studies performed on H3 hemagglutinin subtype from 1968 through 1999 have revealed a total of 101 amino acid mutations (on a total of approximately 560 amino acids), with an average of about 3.5 mutations per year. 60% of mutations which occurred in the studied period were retained in the circulating viruses the following year too, indicative of the persistence of an immune-mediated selective pressure. 95% of these mutations were found in the HA1 hemagglutinin subunit, that is the one directly involved in the binding to sialic acid. Within such a high variability, however, some unchanged amino acid residues have been found, indicative of their essential role in the function of the protein. These hemagglutinin portions represent a potential target for a cross-neutralizing response towards the different subtypes of influenza viruses. However, it is predictable that such regions will not be able to induce an effective antibody response in most patients, since the fact that such targets hide in immunosilent areas has certainly represented a very favorable evolutionary step for the virus.

In fact, when referring to anti-influenza immunity, three different types of immunity must be taken into consideration, which can be well understood in the light of the data reported above HOMOLOGOUS IMMUNITY: related to the individual isolate. This type of immunity is always seen after an infection or a vaccination, but it provides a very limited protection against other isolates.

HOMOSUBTYPE IMMUNITY: related to isolates belonging to the same subtype. This type of immunity is often seen after an infection or a vaccination, but is lost when the mutation rate in hemagglutinin and/or neuraminidase increases considerably.

HETEROSUBTYPE IMMUNITY: related to isolates belonging to different subtypes. This type of immunity is extremely rare both in case of natural infection and in case of vaccination. From the strategic point of view, it is the most important immunity, as its presence and stimulation would be equivalent to the resistance to infection by every type A influenza virus.

Until a few years ago, it was thought that the heterosubtype immunity could be achieved just by stimulating effectively cellular immunity components directed against less mutated viral proteins, such as for example the NP protein that constitutes its core. However, recent studies have shown that mice depleted of CD8 lymphocytes are still able to display a heterosubtype immunity, in contrast with mice depleted of the type B lymphocyte component (Nguyen H H, J Inf. Dis. 2001, 183: 368-376). An even more recent study has confirmed this data, highlighting a crucial role of antibodies, even if not neutralizing, directed precisely against epitopes that are conserved among the different subtypes (Rangel-Moreno et al. The J of Immunol, 2008, 180: 454-463).

OBJECT OF THE INVENTION

On the basis of the data reported above, one object of the present invention is to provide a monoclonal antibody, preferably human or humanized, reactive against the different subtypes of the influenza A virus.

Another object of the present invention is to provide a monoclonal antibody, preferably human or humanized, with neutralizing activity towards multiple subtypes of the influenza A virus.

Such an antibody would be an effective means of prevention when administered to patients at risk. Furthermore, the use of a human or humanized monoclonal antibody for human patients would give a further advantage, as the antibody would certainly be well tolerated.

Secondly, by constituting a component of the human antibody response to this virus, the monoclonal antibody with the above-mentioned features could represent a key factor for the design of innovative vaccines capable of inducing an extremely more effective, protective and broad-range immunity, compared to that induced by the currently used vaccines.

However, the achievement of monoclonal antibodies with such properties has so far proved to be extremely difficult.

The International patent application WO2007/134327, issued on Nov. 22, 2007, describes Fab fragments capable, in ELISA assays, of binding to the HA antigen from various isolates of the influenza A virus, subtype H5. However, this patent application does not provide an enabling description of antibodies capable of recognizing isolates belonging to different subtypes of the influenza A virus, nor does it describe in an enabling way the attainment of antibodies with actual neutralizing abilities towards influenza A viruses belonging to different subtypes.

Therefore, in spite of the fact that a monoclonal antibody with the ability to recognize and neutralize the different subtypes of the influenza A virus has been sought for a long time, such a need has so far remained frustrated.

DESCRIPTION OF THE INVENTION

Figure 1:
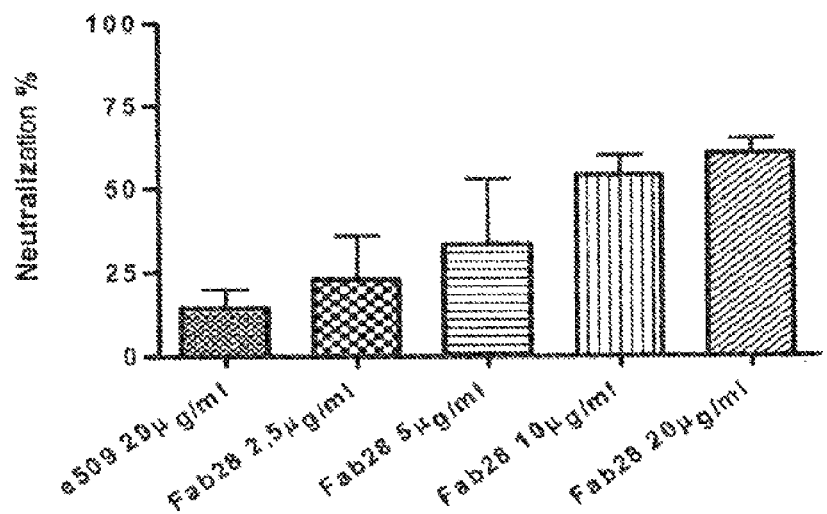
FIG. 1 is a graph that illustrates the neutralization percentage of the virus A/PR/8/34 (H1N1) by different Fab 28 concentrations.

The present inventors have surprisingly succeeded in providing monoclonal antibodies with the above-mentioned desirable features.

Thus, a first object of the present invention is a monoclonal antibody directed against the hemagglutinin antigen of the influenza A virus, characterized by being able to bind multiple subtypes of the influenza A virus.

A second object of the present invention is a monoclonal antibody directed against the influenza A virus, characterized by having a neutralizing activity towards multiple subtypes of the influenza A virus. Preferably, such a neutralizing monoclonal antibody recognizes influenza A virus hemagglutinin (HA) as the antigen.

The monoclonal antibodies of the invention are preferably human or humanized antibodies.

The attainment of human monoclonal antibodies according to the invention and their binding properties are described in detail in the experimental section that follows.

The preparation of humanized antibodies is performed by any per se known methodology, as for example described in Baca et al, 1997 J. Biol. Chem. 272:10678 -84 or Carter et al, 1992, Proc. Natl. Acad. Sci. 89:4285. Such bibliographic references are provided exclusively for illustration and not limitation. In fact, other methodologies for the preparation of humanized antibodies are known in the prior art and can be used within the present invention.

The attainment of 6 clones (designated as INF4, INF16, INF28, INF39, INF43 and INF47) capable of producing monoclonal antibodies in the form of Fab fragments with the in vitro ability of binding multiple influenza A virus subtypes is specifically described in the following experimental section.

The monoclonal antibody produced by clone INF28 (designated as Fab28) represents one preferred embodiment of the invention, as the inventors have experimentally proved that this antibody displays a neutralizing activity towards multiple influenza A virus subtypes. For the sake of brevity, such an immunological property will sometimes be referred to herein below as "heterosubtype cross-neutralizing activity".

The Fab28 antibody is characterized by a heavy chain variable domain with the amino acid sequence SEQ ID NO:1 and a light chain variable domain with the amino acid sequence SEQ ID NO:2. The nucleotide sequence encoding for the heavy chain variable domain is SEQ ID NO:3 and the nucleotide sequence encoding for the light chain variable domain is SEQ ID NO:4.

In particular, the experimental section describes the manufacture of the monoclonal antibodies of the invention as Fab fragments. However, other antibody forms too, and the manufacture and use thereof are intended to be part of the scope of the invention. Non-limiting examples are whole immunoglobulins, or other kinds of antibody fragments, such as for instance $F(ab')_2$ fragments or antibody fragments smaller than Fabs, or peptides that have the same immunological properties as those experimentally demonstrated for the Fab of the invention.

Single chain antibodies can be constructed according to the method described in U.S. Pat. No. 4,946,778 by Ladner et al., hereby included as reference. Single chain antibodies comprise the light and heavy chain variable regions linked by a flexible linker The antibody fragment designated as single domain antibody is even smaller than the single chain antibody, as it comprises only one isolated VH domain. Techniques for obtaining single domain antibodies having, at least partially, the same binding ability as the whole antibody, are described in the prior art. Ward, et al., in "Binding Activities of a Repertoire of Single Immunoglobulin Variable Domains Secreted from *Escherichia coli*," Nature 341:644-646, describes a screening method for obtaining the variable region of an antibody's heavy chain (VH single domain antibody) with a sufficient affinity for the target epitope to bind to it in an isolated form.

In the description that follows, the term "antibody" will then be used to refer to all the embodiments mentioned above, including whole immunoglobulins, Fab fragments or other antibody fragment types, single chain antibodies, single domain antibodies, etc.

The monoclonal antibodies of the invention may be generated and used in a free form or in a carrier-conjugated form. A carrier is any molecule or chemical or biological entity capable of conjugating with an antibody and making it immunogenic or increasing its immunogenicity. Non-limiting examples of carriers are proteins such as KLH (keyhole limpet hemocyanin), edestin, thyroglobulin, albumins as bovine serum albumin (BSA) or human serum albumin (HSA), erythrocytes such as sheep erythrocytes (SRBC), tetanus anatoxin, cholera anatoxin, polyamino acids such as for example poly(D-lysine:D-glutamic acid) and the like. In order to facilitate the binding of the antibody to the carrier, the antibody C-terminus or N-terminus may be modified, for example, by the insertion of additional amino acid residues, for instance one or more cysteine residues that are able to form disulfide bridges.

Because of their properties, which will be shown in detail in the experimental section that follows, the monoclonal antibodies of the invention (especially the antibody Fab28) are particularly suited for use in medical applications, particularly in the manufacture of a medicament for the broad-range prophylactic or therapeutic treatment of influenza A virus infections.

Thus, the use of a monoclonal antibody of the invention, preferably the antibody Fab28, for the manufacture of a medicament for the prophylactic or therapeutic treatment of pathologies caused by influenza A virus infections, such as for instance the influenza syndrome, is within the scope of the invention.

In this context too, the expression "Fab28 antibody" includes not only the Fab fragments but also any other form into which the antibody can be prepared, for example whole immunoglobulins, other kinds of antibody fragments, single chain antibodies, etc.

As described in detail in the experimental section, the monoclonal antibodies have been obtained by molecular biology techniques starting from an EBV-transformed lymphocyte capable of producing cross-reactive monoclonal antibodies, thus able to recognize MDCK cell lysates infected with the two reference isolates as referred to herein below, which belong to different subtypes of the influenza A virus: H1N1, strain A/PR/8/34 and H3N2, strain A/PC/1/73. The specific procedures used to generate the transformed B cell lines from patients' peripheral blood are described in the experimental section.

In addition, the procedures used to clone the genes encoding the heavy and light chain variable portions of the Fab28 antibody of the invention are described in the experimental section, as well as the procedures to produce them recombinantly, both as single peptides and Fab fragments.

The ability of the monoclonal antibodies of the invention to react with cell lysates infected with different influenza A virus subtypes were verified by ELISA and immunofluorescence. In addition, a neutralizing assay was carried out in order to verify the in vitro biological activity of the antibodies. In this assay, the Fab28 antibody showed a heterosubtype cross-neutralizing activity towards the reference type A viral isolates as indicated above.

The obtained data suggest that the antibodies of the invention, especially antibody Fab28, are extremely effective in conferring a passive immunity towards the influenza A virus to the subjects to whom they are administered, and that, accordingly, they are particularly useful in the broad-range prophylactic or therapeutic treatment of influenza A virus infections or pathologies directly or indirectly caused by influenza A virus infection. One example of such pathologies is the influenza syndrome.

In addition, the identification of the hemagglutinin conformational epitope that Fab28 binds to is described in the experimental section. Such a conformational epitope lies between hemagglutinin HA1 region and HA2 region and includes W357 and T358 residues on HA2 region and N336, 1337 and P338 residues on HA1 region. The numbering of the residues is based on the hemagglutinin sequence from H1N1/A/PR/8/34 isolate in the database BLAST (SEQ ID NO: 5).

Thus, a further object of the invention is a pharmaceutical composition comprising an effective amount of a monoclonal antibody of the invention as the active ingredient and a pharmaceutically acceptable carrier and/or diluent. An effective amount is that which is able to induce a favourable effect in the subject to which the composition is administered, for example to neutralize the influenza A virus or interfere with the virus replication.

In this context, the term "subject" designates any animal host to which the composition can be administered, including humans.

Non-limiting examples of useful pharmaceutically acceptable carriers or diluents for the pharmaceutical composition of the invention include stabilizers such as SPGA, carbohydrates (for example, sorbitol, mannitol, starch, sucrose, glucose, dextran), proteins such as albumin or casein, protein-containing agents such as bovine serum or skimmed milk, and buffers (for example phosphate buffer).

The monoclonal antibodies of the invention can also be advantageously used as diagnostic reagents in an in vitro method for the detection of anti-influenza A virus antibodies with identical or similar neutralizing properties in a biological sample previously obtained from a patient (such as for example a serum, plasma, blood sample or any other suitable biological material).

"Anti-influenza A virus antibodies with identical or similar neutralizing properties" are antibodies that display a heterosubtype cross-neutralizing activity versus the influenza A virus. These antibodies may be found in the biological sample from the patient as a result of a previous exposure to an influenza A virus, or because the patient had been previously administered a monoclonal antibody of the invention for therapeutic or prophylactic or research purposes.

An assay method for detecting, in a patient's biological sample, the presence of anti-influenza A virus antibodies having a heterosubtype cross-neutralizing activity, comprising contacting the said biological sample with a monoclonal antibody of the invention, as a specific assay reagent, is thus included in the scope of the invention.

The assay can be a qualitative or quantitative one. The detection or quantification of anti-influenza A virus antibodies having a heterosubtype cross-neutralizing activity may be carried out by, for example, a competitive ELISA assay. Thus, a diagnostic kit comprising a monoclonal antibody according to the invention as a specific reagent is also within the scope of the invention, the said kit being particularly designed for the detection or quantification of anti-influenza A virus antibodies having a heterosubtype cross-neutralizing activity towards the influenza A virus in a biological sample derived from a patient.

Similarly, the monoclonal antibodies of the invention (especially antibody Fab28) can be used as specific reagents in an assay method for detecting or quantifying, in a previously prepared immunogenic or vaccine composition, epitopes capable of evoking, in the subject to which such a composition has been administered, anti-influenza A virus antibodies having neutralizing properties identical or similar to those of the monoclonal antibody of the invention, that is a heterosubtype cross-neutralizing activity towards the influenza A virus.

Such a method is predicted to be useful for the assessment of any preparation to be used as a vaccine or immunogenic preparation, as the recognition by the monoclonal antibody of the invention could be indicative of the presence, in the immunogenic preparation and/or vaccine, of one or more epitopes capable of stimulating the production of antibody clones capable of recognizing an advantageous epitope, such as for example an epitope capable of eliciting a heterosubtype immunity against the influenza A virus.

Finally, the monoclonal antibodies of the invention may be used for the manufacture of anti-idiotype antibodies according to methods per se known. Anti-idiotype antibodies are antibodies specifically directed towards the idiotype of the broad-range neutralizing antibodies used to prepare them, and as such are able to mimic the key epitopes they recognize.

Therefore, anti-idiotype antibodies directed against a monoclonal antibody of the invention are also included in the scope of the invention.

The following experimental section is provided solely by way of illustration and not limitation and does not intend to restrict the scope of the invention as defined in the appended claims. The claims are an integral part of the description.

EXPERIMENTAL SECTION

1. Selection of the Patients

The patients enrolled in the study were selected so as to increase the chances of cloning cross-reactive anti-influenza antibodies, that is antibodies capable of recognizing, and potentially of neutralizing, influenza virus isolates belonging to different subtypes. In particular, it is described that some individuals, despite continuous exposure to the influenza virus (sometimes for professional reasons, as physicians, pediatricians, people working in kindergartens and schools), do not contract the disease. These rare individuals were thought to be less susceptible to influenza virus infection due to the development, for still unknown reasons, of an effective heterosubtype immunity. For this reason they were thought to be the best candidates for the generation of human monoclonal antibodies. In particular, the following inclusion criteria were obeyed: between 25 and 55 years of age; recent pathological medical history, for the ten years preceding the study, negative for clinical influenza syndromes; antibody titer higher than 1:1000 against virus isolates, subtypes H1N1 and H3N2 responsible for the annual epidemics during the five years preceding the study; high neutralizing titer (IC50>=1:400) against virus isolates, subtypes H1N1 and H3N2 responsible for the annual epidemics during the five years preceding the study; detectable neutralizing titer (IC50>=1:20) against two reference subtype A virus isolates (A/PR/8/34 subtype H1N1; A/PC/1/73 subtype H3N2); no prior anti-influenza vaccination; compliance to receive anti-influenza vaccination.

At vaccination, and about 3 weeks post-vaccination, approximately 20 ml of blood were drawn from each patient into heparinized test-tubes.

2. Culture of the Reference Virus Isolates

MDCK (Madin-Darby canine kidney) cells (ATCC® no. CCL-34™) propagated in Modified Eagle Medium (MEM) (GIBCO), supplemented with 10% inactivated fetal bovine serum (FBS) (treatment at 56° C. for 30 minutes) (Euro-Clone), 50 µg/ml penicillin, 100 µg/ml streptomycin (GIBCO) and 2 mM L-glutamine (EuroClone) were used as the cell line. The cells were incubated at 37° C. in a 5% $CO_2$ atmosphere and were passaged at a 1:3 ratio twice a week. For the experiments described in this patent application, the following influenza virus isolates were used: H1N1, strain A/PR/8/34 (ATCC® no. VR-1469™); H3N2, strain A/PC/1/73 (ATCC® no. VR-810), and strain B/Lee/40 (ATCC® no. VR-101). As the culture medium to grow the virus, MEM supplemented with 1 µg/ml serum-free trypsin (SIGMA) was used. The virus stocks were obtained from the culture supernatant as extracellular viruses. In short, after infecting the cells, the monolayer was observed daily to monitor the appearance of a cytopathic effect. Generally 4 days after the infection the supernatant was collected, centrifuged at 1000 RCF (relative centrifugal force) for 10 minutes to eliminate the cell debris and filtered with 0.22 μm filters (MILLIPORE). The supernatant was then aliquoted and stored at −80° C. as cell-free viruses.

3. Selection of Monoclonal Anti-Influenza Virus Antibodies from Peripheral Blood B Lymphocytes The production of monoclonal antibodies from patients was carried out by using a trans-formation method via infection of B lymphocytes with Epstein-Barr virus (EBV), previously described by Cole et al, 1984 Cancer Research 22:2750-2753. The supernatant from the different clones obtained was assessed for the presence of antibodies by ELISA. Clones capable of producing IgG antibodies in the supernatant that are able to react in the ELISA against the cell lysates infected with the two reference isolates, subtypes H1N1 and H3N2, were then selected for a subsequent characterization. In particular, MDCK cells were infected with the aforesaid isolates at a high multiplicity of infection. About 48 hours post-infection, the cells were detached from the flask and washed twice in PBS. The cell pellets were then suspended in 300 μl of lysis solution (100 mM NaCl, 100 mM Tris pH 8 and 0.5% Triton-X) and stored in ice for 20 minutes. The cell debris were centrifuged away at 10000 g for 5 minutes and the supernatant was stored at −20° C. as a protein extract. As for the preparation of the control antigen, non-infected cells were treated in the same way. The supernatant protein concentration was determined in duplicate using the BCA™ Protein Assay Kit (Pierce). Briefly, the sample protein dosage was determined by referring to a standard curve obtained by a series of known-concentration dilutions of bovine serum albumin (BSA). The absorbance of every sample was measured with a spectrophotometer at a wavelength of 540 nm. The lysates so obtained were then used (300 ng per well) to coat an ELISA plate (COSTAR) that was incubated at 4° C. overnight. The following day, the plate was washed with distilled water and blocked with PBS/1% BSA (Sigma) for 45 minutes at 37° C. Then, 40 μl of supernatant from each clone were added to each well, which were incubated for 1 hour at 37° C. After 5 washings (WASHER ETI-SYSTEM, DiaSorin) with PBS/0.5% Tween-20 (Sigma), 40 μl of peroxidase-conjugated anti-human Fc (1:4000 in PBS/1% BSA, Sigma) were added to each well and the plate was incubated for 1 hour at 37° C. After 5 more washings with PBS/0.5 % Tween-20, 40 μA of TMB peroxidase substrate (Pierce) were added to each well. Approximately 15 minutes later, the enzymatic activity was blocked by adding 40 μl of $H_2 SO_4$ and the signal was measured with a spectrophotometer set at 450 nm Special attention was given to the supernatant of six putative clones capable of producing cross-reactive antibodies (designated as cINF4, cINF16, cINF28, cINF39, cINF43 and cINF47, respectively), i.e., capable of recognizing both cell lysates infected with the strain belonging to subtype H1N1 and those infected with the strain belonging to subtype H3N2.

4. Preparation of Fab Fragments from the Cross-Reactive Clones

The genes encoding for the monovalent Fab chains capable of reacting with the influenza virus were cloned into a prokaryotic expression vector. This allows to avoid problems due to instability of antibody-producing cell clones, to better characterize the encoding genes from the molecular point of view, in order to have molecules that are certainly monoclonal at one's disposal, as well as increased amounts of each individual antibody.

The messenger RNA (mRNA) was extracted from the cultured clones and reverse transcribed using an oligo-dT according to methods per se known. The cDNAs encoding the light chain and the Fd fragment (i.e. the heavy chain portion present within the Fab fragment) were then amplified by described methods (CSH press, Phage display manual, ed. D. R. Burton, p. A1.6). The so obtained cDNAs were then cloned into an expression vector per se known, designated as pCb3/CAF (Burioni et al, J. Imm. Meth, 1988). In short, the gene (amplified DNA) encoding the heavy chain Fd portion of each Fab was digested with restriction enzymes XhoI and SpeI (Roche) for 1.5 hours at 37° C., and subsequently inserted into the vector's cloning site for heavy chains, in turn digested with the same enzymes. Instead, the light chains (amplified DNA) were digested with enzymes Sad and XbaI (Roche) and cloned into the vector similarly digested.

The so obtained recombinant constructs for each clone were used to electro-transform E. coli strain XL1 Blue (made competent by cold washings in glycerol), according to standardized protocols for the use of 0.2 cm cuvettes (Voltage: 2500 V; Capacitance: 25 μF; Resistance: 200.OMEGA.). In parallel, the DNA sequences of the light chain variable part and the heavy chain variable part of the selected clones were analyzed. The sequences are those provided in the Sequence Listing. The molecular analysis of the mutational pattern showed a picture ascribable to antigen-induced somatic mutation processes for each of the clones.

5. ELISA Assessment of the Monoclonal Fabs Obtained by Cloning into Pcb3/CAF

At completion of cloning, 40 recombinant bacterial clones for each monoclonal antibody were analyzed by ELISA using crude lysates from bacterial cultures obtained by heat shock. In particular, clones of bacteria transformed with the construct PCb3/CAF were inoculated into 10 ml of SB medium containing ampicillin and tetracycline at 50 μg/ml and 10 μg/ml, respectively, and were grown under shaking at 37° C. until reaching an OD.600=1. Subsequently, a specific inducer (IPTG—isopropylβ-D-thiogalactopyranoside) was added at the final concentration of 1 mM and the culture was left shaking at 30° C. overnight. The cells were lysed by heat shock (3 freeze/thawing rounds, at −80° C. and 37° C., respectively) and then centrifuged to separate the cell debris from the Fab-containing supernatant. The soluble Fabs obtained were assayed by ELISA. 96-Well microtiter plates (Nunc) were coated with lysates from cells infected with the above-mentioned reference virus isolates. Lysates obtained from uninfected cells were used as a negative control. The ELISA plates coated with 300 ng of the lysates obtained as described were then left at 4° C. overnight. The next day, after removal of the unbound antigen, the plates were washed 5 times with PBS, and the unspecific binding sites were blocked with 3% albumin in PBS for 1 hour at 37° C. After removal of the blocking solution, the supernatants of the cell cultures treated as described above and containing the soluble Fabs were added thereto, followed by an incubation step at 37° C. for 2 hours. After 10 washing cycles with PBS/0.05% Tween 20, 40 μl of a 1:700 dilution of a polyclonal preparation of radish peroxidase-conjugated goat anti-human Fab immunoglobulins (Sigma) in PBS/1% BSA was added thereto. After a 1-hour incubation at 37° C. and a further series of 10 washes, the substrate (OPD-o-phenylenediamine) was added to the wells. The plates were then incubated for 30 minutes at room temperature in the dark. The reaction was quenched with 1N sulfuric acid and the optical density was assessed by spectrophotometric reading at 450 nm. All the assayed clones displayed reactivity towards the lysates obtained from the infected cells. One bacterial clone transformed with an expression vector containing a gene pair encoding the light chain of a human antibody and the heavy chain Fd fragment was thus selected for each of the cross-reactive monoclonals. Such bacterial clones are able to produce human Fabs capable of binding both the isolate A/PR/8/34 (H1N1 ) and the isolate A/PC/1/73 (H3N2). These clones (with the relative gene pairs) were named INF4, INF16, INF28, INF39, INF43 and INF47.

6. Purification of the Fabs

The Fabs produced from the above-listed cross-reactive clones (from here on indifferently referred to as "clones" or "Fabs") were thus produced through bacteria transformed with the described expression vector and then immunoaffinity purified with columns composed of a sepharose resin containing the protein G (.about.2 mg/ml), to which a polyclonal preparation of goat antibodies capable of binding human Fabs (PIERCE, Ill.) was covalently linked. In short, a single colony of each clone was inoculated into 10 ml of SB medium containing ampicillin and tetracycline at 50 μg/ml and 10 μg/ml, respectively. The culture, which was grown overnight at 37° C., was sub-inoculated into a flask with 500 ml of SB added with the same concentration of antibiotics as before. The cells, subsequently induced by 1 mM IPTG, were left shaking overnight at 30° C. The culture was centrifuged at 5000 rpm for 25 minutes and the pellet resuspended in PBS was sonicated. A further centrifugation at 18,000 rpm for 25 minutes was necessary in order to remove the cell debris. The supernatant was filtered, and then it was slowly passed through the above-described sepharose column. Thereafter, the resin was washed with 10 PBS volumes, and finally the bound Fabs were eluted with an acidic solution (elution buffer—$H_2O$/HCl pH 2.2). The various fractions collected were neutralized with an appropriate solution (1M Tris pH 9) and concentrated by ultrafiltration (Centricon, Millipore). The purity of the purified Fabs was assessed by running one aliquot on a 12% polyacrylamide/sodium dodecyl sulfate gel (SDS-PAGE). Finally, sequential dilutions of the purified Fabs were assayed by ELISA as described. Into each plate, preparations of monoclonal Fabs directed against HCV E2 glycoprotein were included as negative controls. The results of this experiment confirmed those previously obtained with the bacterial lysates.

7. Immunofluorescence Assessment of the Monoclonal Fabs Obtained by Cloning into PCB3/CAF In order to confirm the data achieved by ELISA, the cross-reactive anti-influenza Fabs were also analyzed by an immunofluorescence assay. Briefly, the cells from the infected cultures were trypsinized and, after two washes in PBS, counted under a microscope with a hematocytometer. The cell suspension was thus used for the preparation of slides by centrifugation in a cytocentrifuge (Cytospin4, Shandon Southern Products) at 90 g for 3 minutes. The so prepared slides each contained a total of $2\times10^5$ cells. Control slides were prepared similarly with uninfected cells. The cells were then fixed and permeabilized at room temperature with a methanol-acetone solution (used at the temperature of −20 ° C.) for 10 minutes. After 3 washes in PBS, the cells were incubated with the different clones (100 μg/ml) for 30 minutes at 37° C. in a humid chamber and subsequently washed three times in PBS. The cells were then incubated for 30 minutes at 37° C. in the humid chamber in the dark with a fluoresceine isothiocyanate-conjugated goat Fab (Sigma) diluted 1:200 in Evans Blue. The slides were examined under a fluorescence microscope (Olympus). A commercial mouse monoclonal (Argene) specific for the M1 influenza virus protein was used as a positive control. An antibody directed against the E2 glycoprotein of the hepatitis C virus (e509; Burioni et al, Hepatology, 1998 ) was used as a negative control. All the recombinant Fabs showed, by immunofluorescence, a reactivity that was specific for both the cells infected with the strain A/PR/8/34 (H1N1) and those infected with the strain A/PC/1/73 (H3 N2). Instead, no fluorescence was seen in uninfected cells, B type strain-infected cells, or cells infected with the negative control antibody.

8. Neutralization Assay

In order to characterize the in vitro biological activity of the selected clones, neutralization assays were designed for the three reference virus isolates used in the study. In short, MDCK cells were seeded into MEM-10% FBS in a 96-well plate ($2\times10^4$ cells/well). Serial dilutions (from $10^{-1}$ to $10^{-8}$) of the virus stocks, obtained as described above, were prepared in maintenance medium (MEM with 2% FBS). Each dilution was repeated six times. When the cultured cells were confluent, the growth medium was removed and 100 μl of each of the virus dilutions were added to each well. After 1 hour at 37° C., the inocula were removed and 200 μl of MEM medium added with 1 μg/ml trypsin were placed into each well. The viral titer, expressed as $TCID_{50}$ (the dose that infects 50% of the cell culture), was calculated by applying Reed-Muench's formula:

$$TCID_{50} = \frac{\text{infectivity} > 50\% - 50\%}{\text{infectivity} > 50\% - \text{infectivity} < 50\%} \times \text{dilution factor}$$

In the light of the obtained data, the virus stock was diluted so as to use a multiplicity of infection (M.O.I.) of approximately 0.01 (1 virus particle per 100 cells) in the neutralization experiment. In the actual neutralization assay, MDCK cells were seeded in a 24-well plate, with each well containing a sterile slide. The neutralization experiment was performed on 80%-90% confluent cells, i.e. about 48 hours after the seeding thereof. Dilutions of the purified Fab fragments were then prepared, so as to attain 2.5 μg/ml, 5 μg/ml, 10 μg/ml and 20 μg/ml final concentrations for each antibody. Corresponding dilutions of the e509 anti-HCV antibody were prepared as a negative control. The various Fab concentrations were then incubated with the same volume of diluted virus stock (M.O.I.: 0.01) for 1 hour at 37° C. 250 μl of the virus-Fab mix were subsequently added to the wells containing the cells. A positive control for the infection was achieved by adding the culture medium alone to the virus stock. The plate was incubated for 1 hour at 37° C. in order to allow the non-neutralized virus to adsorb. The inoculum was then removed and the cells were washed twice with PBS. 1.5 ml of serum-free medium with 1 μg/ml trypsin were added to each well. After a 6-hour incubation at 37° C., the cell monolayer was washed with PBS and fixed with a cold methanol-acetone solution (1:2 ratio, stored at −20° C.) for 10 minutes at room temperature. The fixed cells were washed and incubated with 250 μl of a commercial monoclonal anti-M1 antibody (Argene) for 30 minutes at 37° C. in a humid chamber. The cells were washed with PBS and finally incubated with a fluoresceine-conjugated goat anti-mouse antibody, diluted in Evans blue, for 30 minutes at 37° C. in a humid chamber in the dark. After three washes in PBS, the slides were finally examined under a fluorescence microscope. The Fabs' neutralizing activity was determined by counting the single positive cells and calculating the percentage decrease in the number of infected cells, compared to the positive control infected with the virus alone. The neutralization assays were carried out in three separate sessions for each Fab. Particularly, each clone was assayed against the two different reference type A influenza strains and the reference type B strain mentioned previously. In each experiment, the different Fab dilutions were repeated in triplicate, similarly to what performed for the negative (Fab e509 anti-E2/HCV) and positive (virus and medium without Fabs) controls of infection.

Among the six assayed cross-reactive Fabs, the Fab produced by clone INF28 showed a heterotype cross-neutralizing activity against the type A virus isolates. Instead, no reduction was detected with regard to the infecting ability of type B virus used in the study, confirming the specificity of the neutralizing activity observed. In particular, the Fab produced by clone INF28 (called Fab 28) showed an $IC_{50}$ (the Fab concentration that inhibits 50% of infection by the virus isolate assayed) below 5 µg/ml in the case of subtype H1N1 and of approximately 10 µg/ml in the case of subtype H3N2, i.e. concentrations that are easily obtainable by an in vivo administration of the molecules in question even without taking into account the considerable increase in the neutralizing biological activity usually observed when Fabs are converted into the whole immunoglobulin form, one of the possible pharmaceutical formulations included within the scope of the invention.

Figure 2:
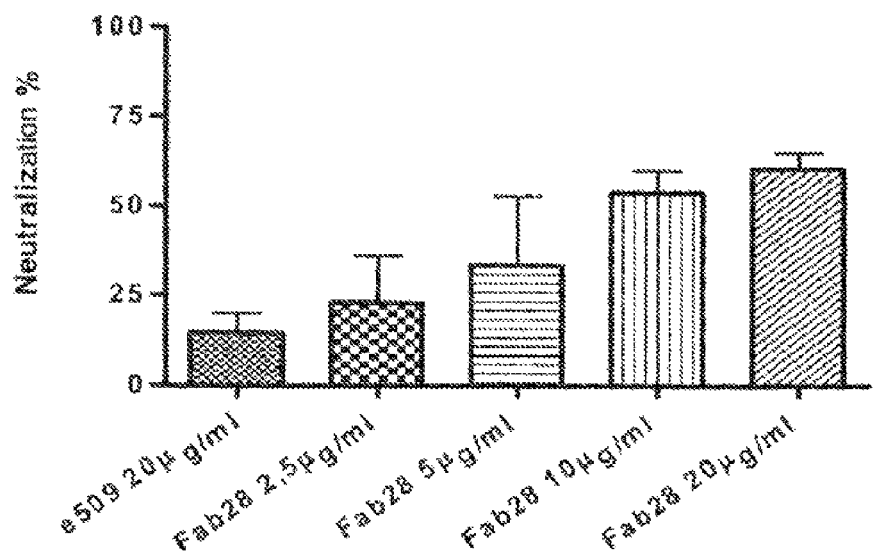
FIG. 2 is a graph that illustrates the neutralization percentage of the virus A/PC/1/73 (HN2) by different Fab 28 concentrations
Figure 3:
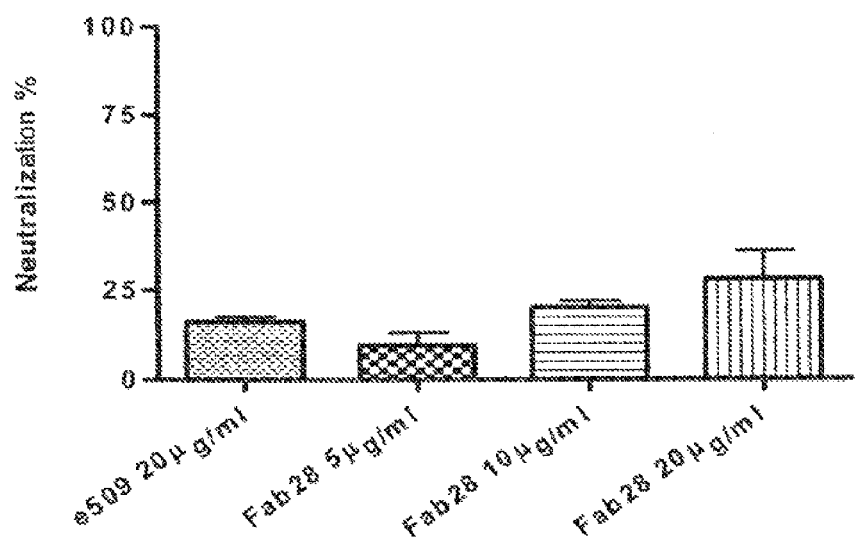
FIG. 3 is a graph that illustrates the neutralization percentage of the virus B/Lee/40 by different Fab 28 concentrations.

FIGS. 1 to 3 summarize the results obtained with Fab 28, produced by clone INF28, in the different neutralization sessions performed on the various influenza virus isolates used in the study. Particularly, FIG. 1 is a graph that illustrates the neutralization percentage of the virus A/PR/8/34 (H1N1) by different Fab 28 concentrations. The results obtained with the human e509 anti-HCV Fab are reported as a negative control. FIG. 2 is a graph that illustrates the neutralization percentage of the virus A/PC/1/73 (H3N2) by different Fab 28 concentrations. The results obtained with the human e509 anti-HCV Fab are reported as a negative control. FIG. 3 is a graph that illustrates the neutralization percentage of the virus B/Lee/40 by different Fab 28 concentrations. The results obtained with the human e509 anti-HCV Fab are reported as a negative control.

9. Characterization of the Antigen Recognized by Fab 28: Western Blot on a Lysate from Infected Cells 10 µg of a cell lysate infected with strain A/PR/8/34 (H1N1), prepared as described earlier, were run under native conditions on a 10% polyacrylamide gel. For this purpose, the samples were run at 100 V for 1 hour in a proper refrigerated tank (BIORAD). Thereafter, the gel was removed from the electrophoresis apparatus and incubated for 10 minutes in Transfer Buffer (Tris base 3 g; Glycine 14.41 g, $dH_2O$ 800 ml, Methanol 200 ml) in order to eliminate any detergent residue. The transfer onto a nitrocellulose membrane (Hybond-ECL; Amersham Biosciences) was then carried out overnight at 30 V and 90 mA. The membrane was then blocked for 1 hour with 5% dried milk dissolved in 1×PBS and thereafter washed three times in 1×PBS—0.1% Tween. During each wash, the membrane was left shaking on a swinging platform for 10 minutes. After which, the different Fabs, diluted in PBS with 5% dried milk, were added at the concentration of 5 µg/ml. Besides Fab 28, the following controls were added: e509 as a negative control; commercial mouse anti-HA whole IgG1 (COVANCE); commercial mouse anti-M1 whole IgG1 (ARGENE); mouse anti-M2 whole IgG1 (ABCAM); human serum diluted 1:200. Each antibody was left shaking for 1 hour at room temperature. Thereafter, the membrane was washed again in PBS as described earlier. The same secondary mouse (1:1000) or human (1:2000) antibodies as described for the ELISA assay were then added, depending on the source of the antibody to be detected. For the detection of the signal, a working solution was prepared by mixing two substrates (SuperSignal® West Pico Chemiluminescent Substrate Pierce) in a 1:1 ratio, being particularly careful not to expose it to sources of light. The nitrocellulose membrane was incubated for 5 minutes with the working solution and then removed and mounted in a HyperCassette (AMERSHAM). This was developed on a Kodak X-ray film in the dark room after the necessary exposure time. The described assay was performed in two different sessions, and in each of them the membrane portion incubated with Fab 28 showed the presence of a band weighing slightly less than 80 KDa, consistent with the weight of the immature form of the viral hemagglutinin (HA0). This was confirmed by the same band being also displayed on the strip incubated with the anti-hemagglutinin control antibody. An analogous band, more intense than the others, was also detected in the membrane portion incubated with human serum. The result of this experiment shows that the antibody is directed against the influenza virus hemagglutinin, perfectly consistent with the neutralization data, since hemagglutinin is known to be the target of the immune neutralizing antibody response.

10. Neutralization Assay by Plaque Reduction Assay

Neutralization assays were carried out by using the plaque assay technique to assess more accurately the neutralizing activity of Fab 28. Firstly, preparations of virus isolates, subtypes H1N1 and H3N2, were quantified by plaque assay with the following protocol. MDCK cells were cultured in six-well plates (Costar) in MEM medium supplemented with penicillin and streptomycin (pen/strep), and enriched with 10% fetal bovine serum (FBS). After the cell monolayer had reached 100% confluence, the wells were washed with PBS and fresh MEM culture medium supplemented with the same antibiotics (pen/strep) and trypsin (1 µg/ml) was added thereto. Serial dilutions of the virus stocks were made in the same wells, and the virus was left to adsorb for 1 hour at 34° C. under a 5% $CO_2$ atmosphere. The medium was then aspirated and two washes with PBS were done. More MEM supplemented with antibiotics, trypsin (1 µg/ml) and 0.8% agarose was gently added at a temperature not over 42° C. After infection, the health condition of the cell monolayer was checked under a phase contrast light microscope, and the plates were incubated at 34° C. under a 5% $CO_2$ atmosphere. 48 hours after infection, the agarose layer was removed, being very careful not to damage the cell monolayer. Thereafter, 70% methanol in water, added with crystal violet (1% w/v), was added to the wells. The plate was incubated with permeabilizer/dye at room temperature for 5 minutes. After incubation, the plate was washed with distilled water at room temperature and left to dry under a laminar flow for 5 minutes. Finally, the PFU (plaque forming units) number was assessed under the phase contrast microscope at 4× magnification. Once the virus titer had been calculated as PFU, the corresponding TCID50 were calculated, and that same titer was compared to the titer of the analogous virus stocks by the end-point limiting-dilution technique.

The above titration allowed for quantification of the viruses for the precise assessment of the activity of Fab 28. Several plates were set up analogously to the above-mentioned procedure for titration by plaque assay. A neutralization mix was thus prepared, which comprised the virus (100 TCID50 per well) and different concentrations of the Fabs that were used (Fab 28 and control Fab). In particular, the assay was performed by testing different concentrations of Fabs (20, 10, 5 and 2.5 μg/ml) against 100 TCID$_{50}$ of the diverse influenza virus strains. The virus/Fab mixtures were then incubated for 1 hour at 34° C. under a 5% CO$_2$ atmosphere. After washing the MDCK cells with PBS, the pre-incubated preparations were transferred into the wells having a 100% confluent cell monolayer, then were incubated for 1 hour at 34° C. under a 5% CO$_2$ atmosphere. The assay was carried out and interpreted as described previously, by comparing the number of plaques obtained in the presence of Fab 28 with those obtained in the presence of the same concentration of the control Fab.

The assays were performed using the following influenza isolates belonging to subtypes H1N1 and H3N2:
H1N1:
A/Malaya/302/54
A/PR/8/34
H3N2:
A/Aichi/68
A/Victoria/3/75
A/Port Chalmers/1/73

The results confirmed the neutralizing activity of Fab 28 towards the influenza viruses H1N1 A/Malaya/302/54 and A/PR/8/34, confirming as well IC$_{50}$ values below 2.5 μg/ml. A heterosubtype neutralizing activity was also confirmed against the influenza viruses H3N2 A/Aichi/68, A/Victoria/3/75 and A/Port Chalmers/1/73 (IC$_{50}$ approximately 20 μg/ml).

11. Identification of the Epitope Recognized by Fab 28

Several approaches were followed to identify the hemagglutinin region recognized by Fab 28, the ability of which to recognize an epitope, though conformational, had already been showed by previous experiments. Indeed, Fab 28 resulted capable of recognizing the protein only in Western blot assays performed under semi-native conditions (0.1% SDS). The same experiments had also pointed out the ability of Fab in recognizing only the immature form of the protein (HA0), but not the individual subunits (HA1 and HA2). Hemagglutination inhibition assays (HAI) had been carried out in parallel, with both chicken erythrocytes and human erythrocytes. Despite the remarkable neutralizing activity, Fab 28 proved to have no HAI activity, suggesting that it did not bind residues implicated in the binding between hemagglutinin and sialic acid.

For better characterization of the epitope, two complementary strategies were followed: selection of random peptide sequences, contained in a phage display library, which were able to bind the Fab 28 monoclonal; and in vitro induction, by selective pressure through Fab 28, of viral variants (escape mutants) capable of escaping the antibody's neutralizing activity.

Selection from the peptide library by the panning technique allowed for the identification of a number of peptides capable of specifically binding the Fab 28 idiotype. All the identified peptides were analyzed in order to generate a consensus sequence. Such a consensus sequence was then used for an in silico analysis of a hemagglutinin crystal belonging to subtype H1N1. By this analysis it was possible to reveal the regions potentially recognized by Fab 28. One epitope in particular was subjected to further analysis, in view of its compatibility with the results found earlier, and with those generated in parallel with the approach by the escape mutants. The epitope is localized on the stem region of hemagglutinin, that is in a portion between regions HA1 and HA2 (data perfectly consistent with the results achieved in the Western Blot and HAI assays). The residues critical for the binding which were identified are the following: W357 and T358 on region HA2; N336; I337; P338 on region HA1 (the numbering of the residues refers to the hemagglutinin sequence from the isolate H1N1/A/PR/8/34 present in the BLAST database) (SEQ ID NO: 5).

The assay by the escape mutants was carried out by serial infections of MDCK cells with 100 TCID50 of H1N1/A/PR/8/34 virus in the presence of 10 μg/ml of Fab 28, i.e. a Fab concentration equivalent to its IC90 against the isolate in question. Only after numerous passages, it was possible to detect infection of the cells in the presence of the Fab, indicative of a mutation occurred in the virus genome. In fact, escape mutants mutated in two residues of region HA2, I361 and D362, were selected, which are adjacent to the region identified by the in silico approach, confirming the hypothesis that this is the region recognized by Fab 28.

What is claimed is:

1. An isolated and recombinant monoclonal antibody directed against the influenza A virus hemagglutinin antigen, the antibody comprising SEQ ID NO: 1 and 2, wherein the monoclonal antibody is capable of binding an influenza A virus subtype containing hemagglutinin H1 and an influenza A virus subtype containing hemagglutinin H3, wherein the isolated and recombinant monoclonal antibody is conjugated to a carrier.

2. The isolated and recombinant monoclonal antibody of claim 1, wherein SEQ ID NO: 1 is encoded by nucleotide sequence SEQ ID NO: 3 and the SEQ ID NO: 2 is encoded by nucleotide sequence SEQ ID NO: 4.

3. The isolated and recombinant monoclonal antibody of claim 1, wherein the isolated and recombinant monoclonal antibody is a human antibody.

4. The isolated and recombinant monoclonal antibody of claim 1, wherein the isolated and recombinant monoclonal antibody has a modified C-terminus or a modified N-terminus.

5. The isolated and recombinant monoclonal antibody of claim 1, wherein the isolated and recombinant monoclonal antibody has one or more amino acid residues capable of forming disulfide bridges.

6. An isolated polypeptide selected from SEQ ID NO: 1 and SEQ ID NO: 2.

7. A diagnostic kit comprising the isolated and recombinant monoclonal antibody of claim 1.

8. The isolated and recombinant monoclonal antibody of claim 1, wherein the antibody is selected from the group consisting of: whole immunoglobulins and immunoglobulin fragments comprising SEQ ID NO: 1 and SEQ ID NO: 2.

9. The isolated and recombinant monoclonal antibody of claim 8, Wherein the immunoglobulin fragments are selected from the group comprising Fab fragments, Fab' fragments, $F(ab')_2$ fragments, Fv fragments, and single chain antibodies (scFv).

* * * * *